United States Patent
Yonezu et al.

(10) Patent No.: US 9,322,680 B2
(45) Date of Patent: Apr. 26, 2016

(54) GAS SENSOR

(71) Applicant: NGK SPARK PLUG CO., LTD., Nagoya-shi, Aichi (JP)

(72) Inventors: Kunihiko Yonezu, Mie-ken (JP); Toshiya Matsuoka, Kaizu (JP); Norimasa Osawa, Inuyama (JP); Hisaharu Nishio, Tokai (JP); Tomohiro Tajima, Kasugai (JP)

(73) Assignee: NGK SPARK PLUG CO., LTD., Aichi (JP)

( * ) Notice: Subject to any disclaimer, the term of this patent is extended or adjusted under 35 U.S.C. 154(b) by 370 days.

(21) Appl. No.: 13/901,179

(22) Filed: May 23, 2013

(65) Prior Publication Data

US 2013/0312485 A1 Nov. 28, 2013

(30) Foreign Application Priority Data

May 24, 2012 (JP) .................................. 2012-118872
May 20, 2013 (JP) .................................. 2013-105767

(51) Int. Cl.
*G01D 11/30* (2006.01)
*G01N 27/407* (2006.01)

(52) U.S. Cl.
CPC ............ *G01D 11/30* (2013.01); *G01N 27/4078* (2013.01)

(58) Field of Classification Search
CPC ............................ G01D 11/30; G01N 27/4078
USPC .................................... 73/23.31; 204/424, 426
See application file for complete search history.

(56) References Cited

U.S. PATENT DOCUMENTS

| | | | | |
|---|---|---|---|---|
| 8,806,918 B2* | 8/2014 | Yonezu | .............. | G01N 27/4077 204/424 |
| 2009/0200164 A1* | 8/2009 | Yoshikawa | ........... | G01N 27/407 204/406 |
| 2013/0074578 A1* | 3/2013 | Yonezu | .............. | G01N 27/4077 73/23.31 |
| 2014/0020446 A1* | 1/2014 | Yonezu | .............. | G01N 33/0009 73/23.2 |
| 2014/0174165 A1* | 6/2014 | Magera | ................ | G01M 15/04 73/114.31 |
| 2014/0311212 A1* | 10/2014 | Boyd | ................ | G01N 27/4078 73/23.2 |

FOREIGN PATENT DOCUMENTS

JP         2011-145267 A         7/2011

* cited by examiner

*Primary Examiner* — Daniel S Larkin
(74) *Attorney, Agent, or Firm* — Sughrue Mion, PLLC (57) ABSTRACT

A thin plate member which has a groove portion recessed toward the inside in a radial direction with a gap interposed between the thin plate member and the outer surface of a site on the front end side of a main body section. At least one end of the thin plate member is joined to the outer surface of the main body section and is provided radially outside the site on the front end side of the main body section. A seal member is disposed in the groove portion and has elasticity due to resin. Since the gap functions as a heat-insulating layer and is interposed between the seal member and the main body section, heat conduction from the main body section, that is, heat conduction through a first pathway is reduced, and thus deterioration of the seal member due to heat is suppressed.

12 Claims, 8 Drawing Sheets

FIG. 8E ic
GAS SENSOR

BACKGROUND OF THE INVENTION

1. Field of the Invention

The present invention relates to a gas sensor provided with a gas sensor element that detects the concentration of gas to be measured.

2. Description of the Related Art

Conventionally, as a gas sensor, a sensor which is provided with a sensor element in which electrical characteristics change depending on the concentration of a specific gas component in gas to be measured is known. Such a gas sensor is provided with, for example, a tubular metal shell which retains the sensor element, a tubular external cylinder which is swaged and fixed to the circumference of a rear end portion of the metal shell, and a seal member which is disposed in a groove portion formed in the outer peripheral surface of the metal shell.

If the gas sensor is inserted into a mounting hole formed in a mounting target body that is a target on which the gas sensor is mounted, from the front end side thereof, the seal member is deformed by being pressed against an inner wall of the mounting hole by a pressing force at the time of gas sensor mounting and performs sealing between the mounting target body and the external cylinder.

JP-A-2011-145267 is an example of the related art.

3. Problems to be Solved by the Invention

However, in general, since the metal shell is located close to the gas sensor element and made of metal, the metal shell is easily affected by heat generation of the gas sensor element. As a result, the temperature of the metal shell exceeds the heatproof temperature of the seal member made of resin, and thus a problem arises in that the durability of the seal member decreases. In order to maintain the durability of the seal member, the usage environment should be adjusted, and thus a usable environmental condition is limited.

Such a problem is a common problem arising in not only a so-called vertical type gas sensor in which a connector for extracting a signal that represents the concentration of a gas component extends along the direction of an axial line, but also in a so-called horizontal lead-out type gas sensor in which a connector extends in a direction intersecting an axial line.

SUMMARY OF THE INVENTION

The present invention has been made in view of the above-described problems, and other problems not described above, and has an object to suppress heat transfer to a seal member, thereby suppressing deterioration of the seal member.

The invention has been made in order to address at least some of the above-described problems and can be realized as the following forms or application examples, but is not limited thereto.

According to first aspect of the invention, there is provided a gas sensor including: a gas sensor element having a detecting portion which detects a specific gas component in gas to be measured, wherein the detecting portion is disposed at a front end side in a direction of an axial line of the gas sensor element; a main body section which surrounds a circumference in a radial direction of the gas sensor element, wherein a front end side portion of the main body section is configured to be inserted into a gas sensor mounting hole of a mounting target body, and wherein a rear end side portion of the main body section is configured to be disposed outside the gas sensor mounting hole when the gas sensor is mounted on the mounting target body; a thin plate member which is disposed radially outside the front end side portion of the main body section with a gap interposed between the thin plate member and an outer surface of the front end side portion of the main body section, wherein at least one end of the thin plate member is joined to an outer surface of the main body section; and a seal member which is disposed at the thin plate member and which is brought into pressure contact with the mounting target body when the gas sensor is mounted on the mounting target body.

According to a gas sensor of the first aspect, the gas sensor includes the thin plate member which is disposed radially outside the front end side portion of the main body section with the gap interposed between the thin plate member and the outer surface of the front end side portion of the main body section and is joined to the outer surface of the main body section, and the seal member, which is brought into pressure contact with the inner wall of the gas sensor mounting hole when the gas sensor is mounted on the mounting target body, is disposed at the thin plate member. Therefore, conduction of heat of the gas sensor element to the thin plate member can be suppressed by the gap, that is, an air layer formed between the thin plate member and the main body section. Further, since the thin plate member is formed in the shape of a thin plate, heat-transfer performance from the main body section to the thin plate member can be reduced. Accordingly, deterioration of the seal member due to thermal influence by heat generation of the gas sensor element can be suppressed.

In the gas sensor according to a second aspect of the invention, the main body section may have a metal shell which surrounds the circumference in the radial direction of the gas sensor element, wherein a front end side of the metal shell is configured to be inserted into the gas sensor mounting hole of the mounting target body when the gas sensor is mounted on the mounting target body, and the thin plate member may be joined to the metal shell.

According to the gas sensor of the second aspect, since the thin plate member is mounted on the metal shell, heat generated in the gas sensor element is transmitted to the seal member through the metal shell and the thin plate member. Therefore, it is possible to make a pathway through which heat is transmitted from the gas sensor element to the seal member long as compared to a case where the thin plate member is not provided. Accordingly, thermal insulation performance from the main body section to the seal member can be improved.

In a gas sensor according to a third aspect of the invention, the metal shell may have a brim portion which protrudes toward the outside in the radial direction of the gas sensor element, and one end of the thin plate member may be joined to a surface on the front end side of the brim portion.

According to the gas sensor of the third aspect, since one end of the thin plate member is joined to the front end surface of the brim portion of the metal shell, the metal shell is supported by the thin plate member. Therefore, thermal insulation performance from the main body section to the seal member can be improved, and even if the weld strength between the metal shell and the thin plate member is reduced, and thus peel-off occurs in a joining portion, falling of the metal shell into the mounting hole of the mounting target body can be suppressed.

In a gas sensor according to a fourth aspect of the invention, the main body section may have a metal shell which surrounds the circumference in the radial direction of the gas sensor element, wherein a front end side of the metal shell is configured to be inserted into the gas sensor mounting hole of the mounting target body when the gas sensor is mounted on the mounting target body, and a cover may be disposed on the rear end side of the metal shell. The gas sensor further includes a tubular base body which is joined to an outer periphery on a rear end portion of the metal shell and which connects the metal shell and the cover The thin plate member may be joined to the tubular base body.

According to the gas sensor of the fourth aspect, the thin plate member is joined to the base body disposed between the metal shell and a cover section. Therefore, it is possible to make a heat transfer pathway from the gas sensor element to the seal member long and it is possible to interpose a plurality of members in the heat transfer pathway. Accordingly, thermal insulation performance from the main body section to the seal member can be improved.

In a gas sensor according to a fifth aspect of the invention, the main body section may have a metal shell which surrounds the circumference in the radial direction of the gas sensor element, wherein a front end side of the metal shell is configured to be inserted into the gas sensor mounting hole of the mounting target body when the gas sensor is mounted on the mounting target body. The gas sensor further includes a flange which is attached to the metal shell and which is configured to be attached to the mounting target body. The thin plate member may be attached to the flange.

According to the gas sensor of the fifth aspect, since the thin plate member is assembled to the flange, it is possible to make a heat transfer pathway from the gas sensor element to the seal member long and it is possible to interpose a plurality of members in the heat transfer pathway. Accordingly, thermal insulation performance from the main body section to the seal member can be improved.

In a gas sensor according to a sixth aspect of the present invention, the main body section may have a metal shell which surrounds the circumference in the radial direction of the gas sensor element, wherein a front end side of the metal shell is configured to be inserted into the gas sensor mounting hole of the mounting target body when the gas sensor is mounted on the mounting target body A cover is disposed on the rear end side of the metal shell, and the cover may have a signal extraction section which extends in a direction intersecting the direction of the axial line.

The gas sensor of the sixth aspect is configured as a so-called horizontal lead-out type gas sensor in which the cover has the signal extraction section formed to extend in a direction intersecting the direction of the axial line of the gas sensor. In the horizontal lead-out type gas sensor, since a reduction in size to reduce a height in the direction of the axial line is desired in order to secure the degree of freedom of a disposition layout, it is easy for a seal member and a heat generation site of a gas sensor element to come close to each other. However, according to the gas sensor of the sixth aspect, an air layer can be interposed between the main body section which directly receives thermal influence of heat generation of the gas sensor element and the seal member. Accordingly, deterioration of the seal member due to thermal influence by heat generation of the gas sensor element can be suppressed.

In a gas sensor according to a seventh aspect of the invention, the thin plate member may comprise a tube portion which is disposed so as to surround a circumference in the radial direction of the main body section, and a bend portion which extends from a rear end of the tube portion toward the outside in the radial direction of the main body section. The seal member may be disposed in contact with the bend portion.

According to the gas sensor of the seventh aspect, since the seal member is disposed in contact with the bend portion, a variation in the manufacturing is reduced.

In a gas sensor according to an eighth aspect of the invention, the thin plate member may have a groove portion recessed toward the inside in the radial direction of the main body section, and the seal member may be disposed within the groove portion.

According to the gas sensor of the eighth aspect, since the seal member is positioned by the groove portion, a variation in the manufacturing is reduced.

In a gas sensor according to a ninth aspect of the invention, the groove portion may be formed at a position distant from a joining portion where the thin plate member and the outer surface of the main body section are joined to each other.

According to the gas sensor of the ninth aspect, the groove portion is formed at a position distant from the joining portion where the thin plate member and the outer surface of the main body section are joined to each other. Therefore, it is possible to make a heat transfer pathway from the main body section to the groove portion long, and thus thermal insulation performance from the main body section to the seal member can be improved.

In a gas sensor according to a tenth aspect of the invention, the thin plate member may comprise a tube portion which is disposed so as to surround a circumference in the radial direction of the main body section, wherein the tube portion comprises a front end portion; and a bend portion which extends from a rear end of the front end portion of the tube portion toward the outside in the radial direction of the main body section. The seal member may be disposed in contact with the bend portion.

According to the gas sensor of the tenth aspect, since the seal member is disposed in contact with the bend portion, a variation in the manufacturing is reduced.

In a gas sensor according to an eleventh aspect of the invention, the thin plate member may comprise a tube portion which is disposed so as to surround a circumference in the radial direction of the main body section, wherein the tube portion comprises a through-hole. The seal member may be configured to be fitted into the through-hole.

According to the gas sensor of the eleventh aspect, since the seal member is configured to be fitted into the through-hole, it becomes possible to broaden the options of a mounting place.

In a gas sensor according to a twelfth aspect of the invention, one end of the thin plate member may be joined to the outer surface of the main body section and the other end of the thin plate member may not be joined to the outer surface of the main body section.

According to the gas sensor of the twelfth aspect, one of the end portions of the thin plate member is not joined and is in an open state. Therefore, it is possible to take in external air from the open portion and air in the gap can be cooled by the external air. Accordingly, thermal insulation performance between the gas sensor element and the seal member can be improved.

In the invention, various aspects described above can be applied with the aspects appropriately combined or some of the aspects omitted.

DETAILED DESCRIPTION OF ILLUSTRATIVE EMBODIMENTS

Illustrative embodiments are described in detail below with reference to the drawings. However, the present invention should not be construed as being limited thereto.

A. FIRST EXAMPLE

A1. Configuration of Gas Sensor 200

Figure 1:
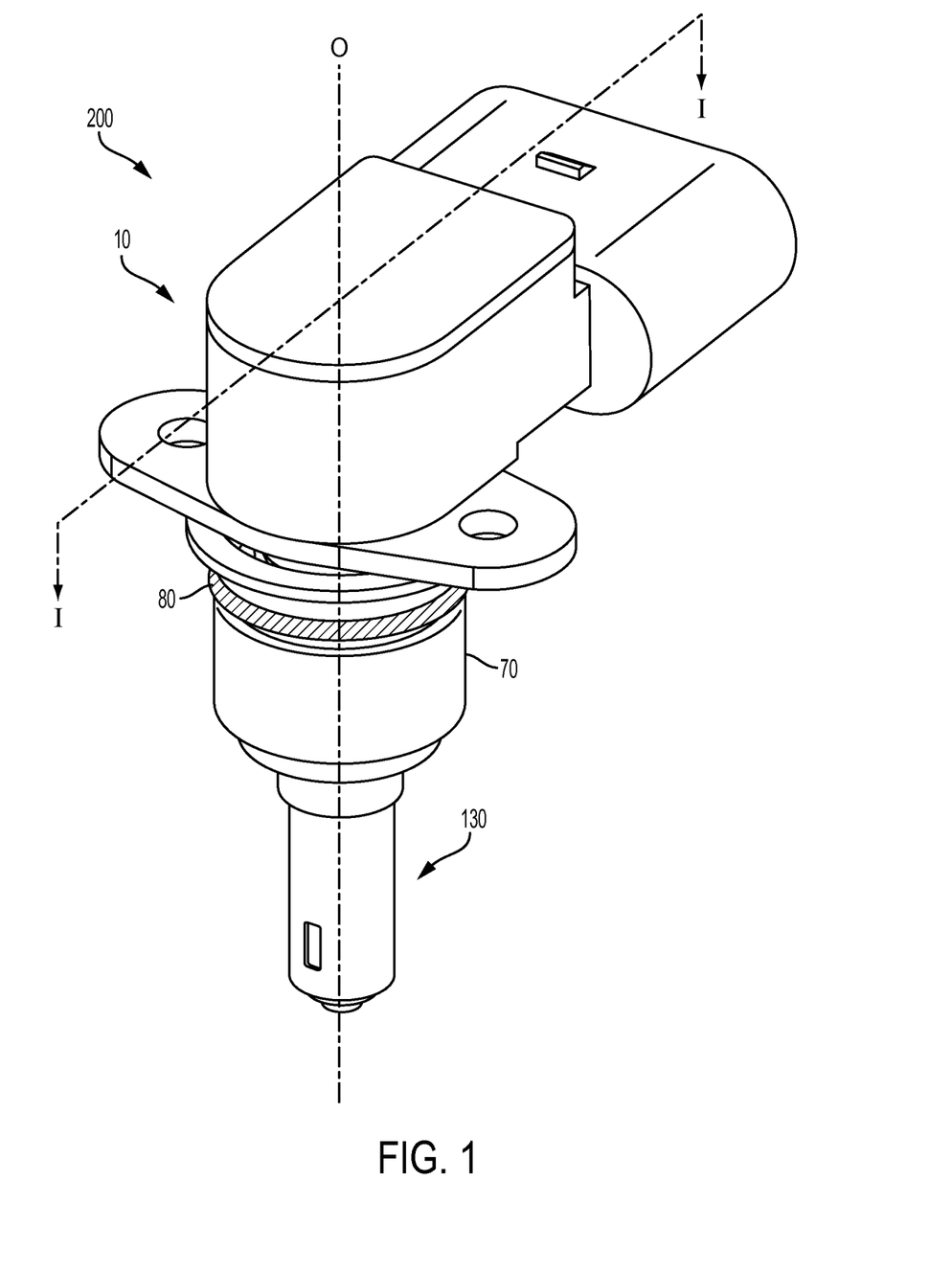
FIG. 1 is a perspective view showing the external appearance of a gas sensor 200 in a first example.
Figure 2:
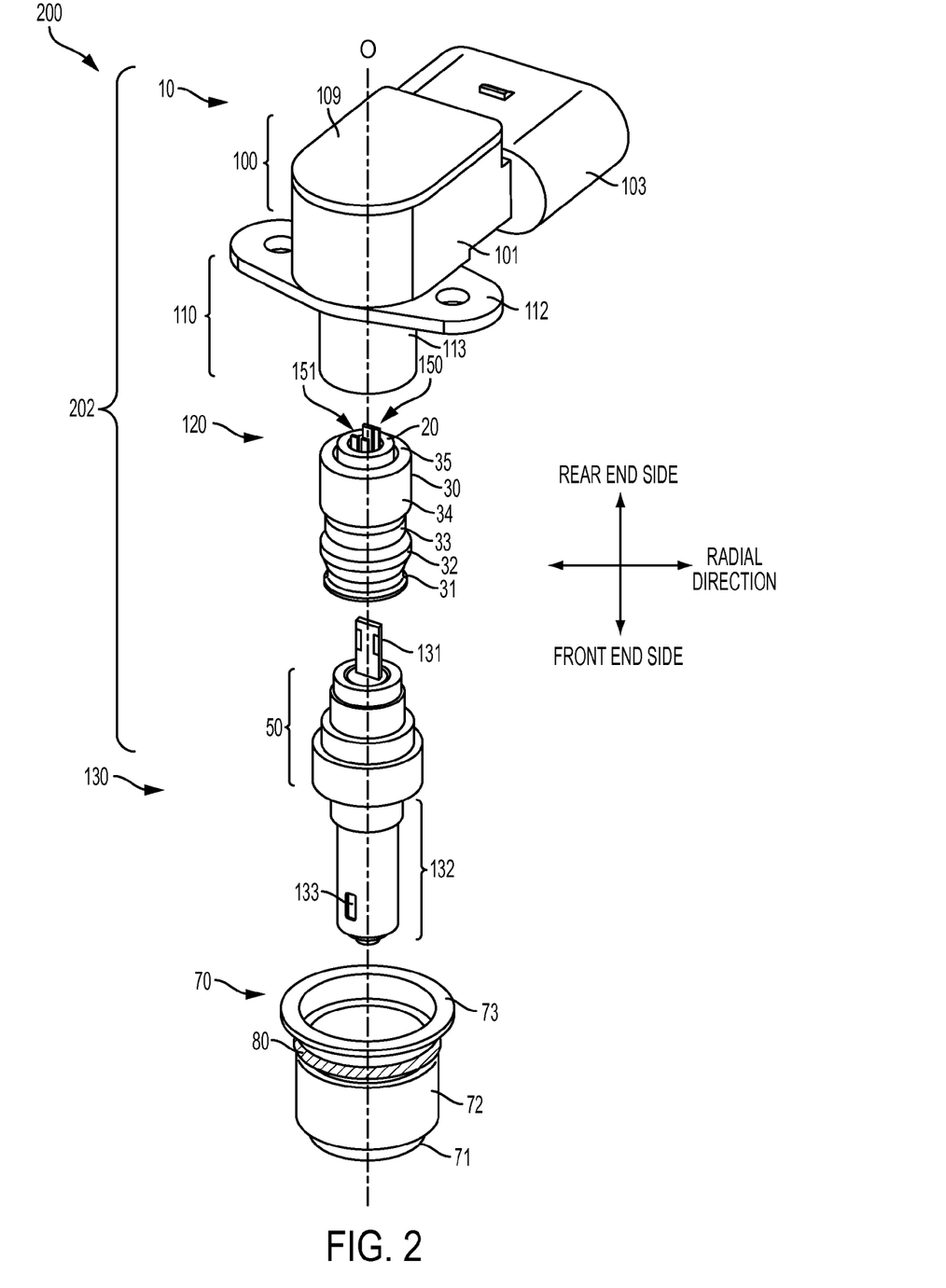
FIG. 2 is an exploded perspective view of the gas sensor 200 in the first example.
Figure 3A:
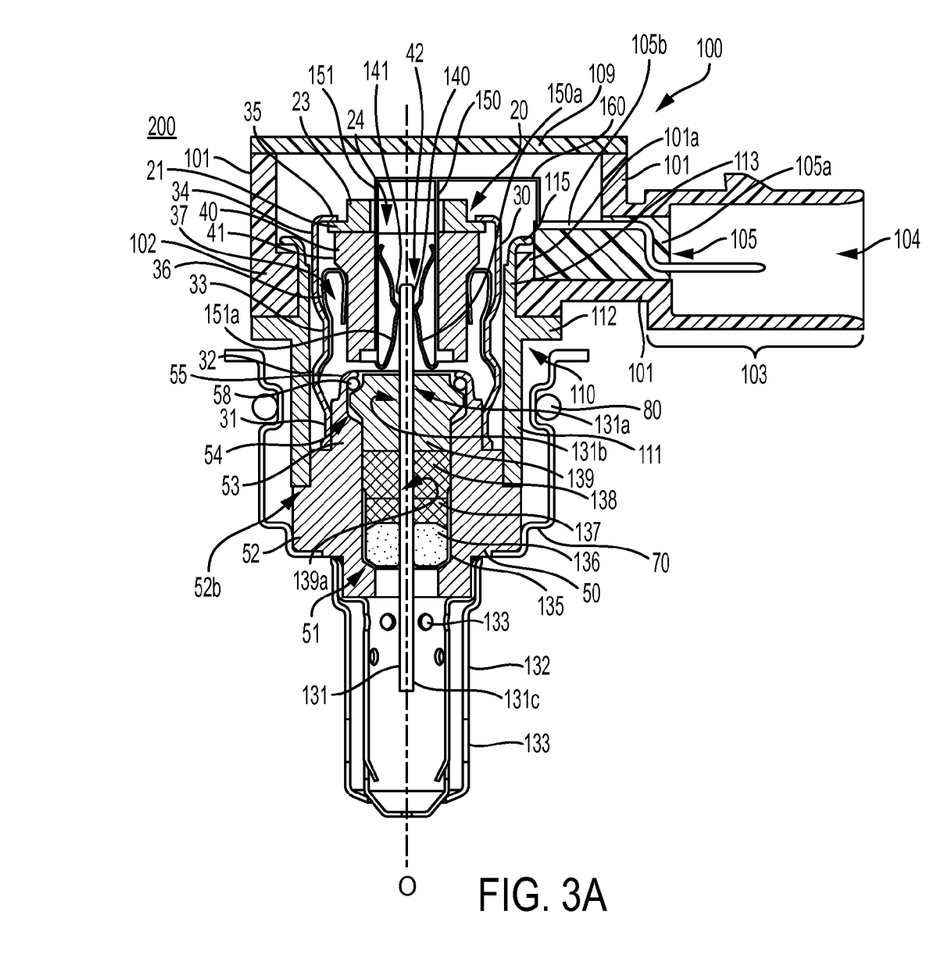
FIGS. 3A and 3B are cross-sectional views of the gas sensor 200 in the first example.
Figure 3B:
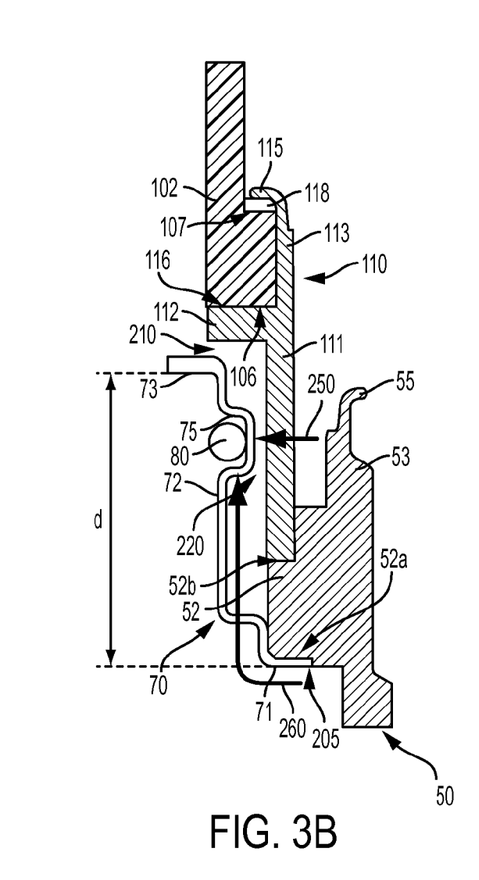

FIG. 1 is a perspective view showing the external appearance of a gas sensor 200 in the first example. FIG. 2 is an exploded perspective view of the gas sensor 200 in the first example. FIGS. 3A and 3B are cross-sectional views of the gas sensor 200 in the first example. FIG. 3A shows a cross section along line I-I of FIG. 1. As shown in FIGS. 1 and 2, the gas sensor 200 includes a cover section 10, a separator assembly 120, an element assembly 130, and a thin plate member 70. A seal member 80 is mounted on the thin plate member 70. The gas sensor 200 has a main body section 202 which includes a metal shell 50 (described later) and the cover section 10. In this example, the direction of an axial line O (equal to an axial line of a gas sensor element 131 and shown by a dashed-dotted line) of the element assembly 130 is illustrated as a vertical direction, and the upper side of the drawing and the lower side of the drawing will be respectively described as the rear end side of the gas sensor 200 and the front end side of the gas sensor 200. Further, a direction perpendicular to the direction of the axial line O is referred to as a "radial direction".

A1-1. Schematic Configuration of Element Assembly 130

The element assembly 130 includes the metal shell 50 having a tubular shape and extending in the direction of the axial line O, the gas sensor element 131 which has the shape of a thin plate and is fixedly disposed inside the metal shell 50, and a protector 132 which covers the front end side of the gas sensor element 131, as shown in FIGS. 2, 3A, and 3B. The gas sensor element 131 has a first plate surface 131*a* extending in the direction of the axial line O, and a second plate surface 131*b* formed on the opposite side to the first plate surface across the axial line O.

A detecting portion 131*c* protruding from the metal shell 50 and configured so as to be able to detect oxygen concentration in exhaust gas is provided on the front end side of the gas sensor element 131. In order to protect the detecting portion 131*c*, the protector 132 having the form of a bottomed double tube is fixed to the front end side of the metal shell 50 by laser welding so as to cover the front end side of the gas sensor element 131, which protrudes from the metal shell 50. In the protector 132, a plurality of introduction holes 133 are formed at predetermined positions so as to be able to introduce exhaust gas to the inside when the gas sensor 200 has been installed in an exhaust pipe.

The rear end side of the gas sensor element 131 protrudes from the metal shell 50 toward the separator 40 side. On the rear end side of the gas sensor element 131, three electrode pads 140 for a sensor electrically conducting the detecting portion 131*c* are provided on the first plate surface 131*a* side and two electrode pads 141 for a heater electrically conducting a heater (illustration is omitted) which is present in the gas sensor element 131 are provided on the second plate surface 131*b*.

As shown in FIGS. 3A and 3B, a step portion 51 in which an inner diameter is reduced toward a direction of a front end is formed on the inner surface of the metal shell 50. Further, the metal shell 50 has a brim portion 52 which protrudes toward the outside in the radial direction, a step portion 53 which is formed further toward the rear end side than the brim portion 52 and reduced in diameter in a stepwise manner, and a rear end portion 55 which is formed on the further rear end side of the step portion 53 and formed in a shape bent toward the inside in the radial direction. The internal configuration of the metal shell 50 will be described in detail later.

A1-2. Detailed Configuration of Separator Assembly 120

The separator assembly 120 is configured to include a grommet 20, the separator 40, a metallic external cylinder 30, a retaining member 36, and connection terminals 150 and 151 and disposed on the rear end side of the metal shell 50. The separator assembly 120 has a swaged portion 33 which is swaged toward the inside in the radial direction from the outside in the radial direction at a substantially central portion in the direction of the axial line O, thereby integrally fixing the metallic external cylinder 30 and the retaining member 36 to each other.

The grommet 20 is an elastic member made of fluorine-containing rubber and having a cylindrical portion 23, a brim portion 21, and an opening 24 and is disposed on the rear end side of the separator 40. The connection terminals 150 and 151 are inserted in the opening 24 of the grommet 20. The opening 24 communicates with an opening 42 of the separator 40 which will be described later.

The separator 40 is formed in a substantially cylindrical shape by resin and has a brim portion 41 formed in a form protruding toward the outside in the radial direction and the opening 42 penetrating in the direction of the axial line O.

The respective connection terminals 150 and 151 are inserted into the opening 42 of the separator 40 and respectively connected to the respective electrode pads of the gas sensor element 131. Hereinafter, in this regard, detailed description will be made. As shown in FIG. 2, the metallic external cylinder 30 having a tubular shape is swaged in a circumferential direction and fixed to the rear end side of the metal shell 50 by laser welding, and the separator 40 is disposed inside the metallic external cylinder 30. The three connection terminals 150 for a sensor and the two connection terminals 151 for a heater are disposed in the separator 40 and accommodated in the separator 40 in a state where the connection terminals 150 for the sensor and the connection terminals 151 for the heater are isolated from each other so as not to come into contact with each other.

The rear end side of the gas sensor element 131 is inserted in the opening 42 of the separator 40. Then, the connection terminals 150 for a sensor are electrically connected to the electrode pads 140 for a sensor of the gas sensor element 131 by coming into elastic contact with the electrode pads 140 for the sensor by an elastic force which is generated due to the shape of a contact portion 150*a* which comes into contact with the electrode pad 140 for the sensor. Further, the connection terminals 151 for a heater are electrically connected to the electrode pads 141 for a heater of the gas sensor element 131 by coming into elastic contact with the electrode pad 141 for the heater by an elastic force which is generated due to the shape of a contact portion 151a which comes into contact with the electrode pad pads for the heater.

The metallic external cylinder 30 has a front end portion 31, tube portions 32 and 34, and a rear end 35. The metallic external cylinder 30 is swaged to the metal shell 50 at the front end portion 31 and welded and joined to the metal shell 50, thereby being fixed to the metal shell 50. Further, the metallic external cylinder 30 is engaged with the brim portion 21 of the grommet 20 at the rear end 35 formed in a shape bent toward the inside in the radial direction.

The retaining member 36 is a metallic tubular member which is fixed to the inside of the metallic external cylinder 30, and biases the separator 40 toward the inside in the circumferential direction and also biases the brim portion 41 of the separator 40 toward the rear end side in the direction of the axial line 0 by an elastic force of a rear end portion 37 formed in the shape of a bend. The retaining member 36 is fixed to the metallic external cylinder 30 by the swaged portion 33 which is formed by being swaged toward the inside in the radial direction from the outside of the metallic external cylinder 30 along with the metallic external cylinder 30.

The separator 40 is not directly fixed to the metal shell 50 and the metallic external cylinder 30 and is retained and fixed in the metallic external cylinder 30 by the metallic external cylinder 30 and the retaining member 36. With such a configuration, poor contact between the connection terminals 150 and 151 and a connector terminal 105b due to vibration or a shift of the separator 40 by vibration or an impact to the gas sensor 200 is suppressed.

A1-3. Detailed Configuration of Cover Section 10

The cover section 10 includes a cover 100 and a metal member 110. The cover 100 includes a resin external cylinder 101 which is made of resin, formed in a substantially tubular shape so as to cover the circumference of the separator assembly 120, and has a brim portion 102 formed in a form protruding toward the inside in the radial direction on the front end side thereof, a lid section 109 which is assembled to the rear end side of the resin external cylinder 101 and blocks the rear end side of the gas sensor 200, and a connector section 103 having a substantially rectangular shape and formed so as to extend in the radial direction from the resin external cylinder 101 at the rear end side of the gas sensor 200. In addition, the connector section 103 is equivalent to a "signal extraction section" in the claims and the metal member 110 is equivalent to a "base section" in the claims.

The resin external cylinder 101 and the connector section 103 are formed of resin having good formability, for example, Nylon (registered trademark), PA (polyamide), PBT (polybutylene terephthalate), or PPS (polyphenyl sulfide). A locking wall 101a which defines the position of a connector terminal section 105 is formed on the connector section 103 side of the resin external cylinder 101. The connector section 103 has an opening portion 104 at an end portion distant from the element assembly 130.

The metal member 110 has a first tube portion 111 formed on the front end side thereof, two semicircular flange portions 112 which are formed on the rear end side of the first tube portion 111 and extend toward the outside in the radial direction, a second tube portion 113 formed on the rear end side of the flange portion 112, and a bend portion 115 formed on the rear end side of the second tube portion 113 and formed in a shape bent toward the outside in the radial direction.

As shown in FIG. 3B, a front end surface 106 of the resin external cylinder 101 is disposed so as to come into contact with a rear end surface 116 of the flange portion 112 and the bend portion 115 is locked to a rear end 107 of the brim portion 102 with a packing 118 interposed therebetween, whereby the resin external cylinder 101 and the metal member 110 are integrally assembled to each other. Then, the metal member 110 and the metal shell 50 are joined to each other in a state where a front end of the first tube portion 111 of the metal member 110 abuts onto a rear end surface 52b of the brim portion 52 of the metal shell 50. The outer diameter of the first tube portion 111 is the same as the outer diameter of the brim portion 52 of the metal shell 50, and if the first tube portion 111 is joined to the brim portion 52 of the metal shell 50, the outer surfaces of the first tube portion 111 and the brim portion 52 of the metal shell 50 become flush. When the resin external cylinder 101 and the metal member 110 are assembled to each other, the packing 118 improves seal performance in an assembled portion and also suppresses damage to the assembled portion.

In a swaging method which is conventionally used in fixation of a resin external cylinder, a brim portion of the resin external cylinder 101 is formed in a form protruding toward the outside in the radial direction and the brim portion is swaged toward the inside in the radial direction from the outside in the radial direction by a swaging member. For this reason, the swaging member has to be formed so as to have a larger diameter in the radial direction than the brim portion, thereby leading to an increase in the size of a gas sensor. Further, in the conventional swaging method, in a horizontal lead-out type gas sensor which is provided with the connector section 103 extending in the radial direction, the connector section 103 becomes an obstacle, and thus swaging is only partially performed and cannot be performed over the entire circumferential direction. For this reason, the resin external cylinder cannot be solidly fixed, and thus there is a concern that damage to the gas sensor 200 may be caused.

In the first example, since the brim portion 102 is formed in a form protruding toward the inside in the radial direction, the metal member 110 can be fixed to the brim portion 102 by being swaged toward the outside in the radial direction from the inside in the radial direction in the inside of the resin external cylinder 101, and thus an increase in the size of the gas sensor 200 can be suppressed and the resin external cylinder 101 and the metal member 110 can be solidly fixed to each other by a simple method such as swaging.

The connector terminal section 105 includes an insulator 105a formed in a substantially rectangular shape and the connector terminal 105b. The connector terminal section 105 is inserted into the gas sensor 200 through the opening portion 104 until the connector terminal section 105 abuts onto the locking wall 101a such that the insulator 105a is gripped by the resin external cylinder 101. The connector terminal 105b connects the opening portion 104 and an intermediate connection terminal 160. The intermediate connection terminal 160 is connected to the rear end portions of the connection terminals 150 and 151, extends in the radial direction from the connection terminals 150 and 151, is bent at a substantially right angle in the direction of the axial line O, and is welded and joined to the connector terminal 105b at an end portion different from an end portion which is connected to the connection terminals 150 and 151. Contact portions between the intermediate connection terminal 160 and the connection terminals 150 and 151 are joined to each other in advance by a method such as welding.

If the cover 100 is assembled to the metal shell 50, the rear end side of the element assembly 130 and the separator assembly 120 are accommodated inside the cover 100 and covered by the resin external cylinder 101 and the connector terminal section 105.

A1-4. Detailed Configurations of Thin Plate Member 70 and the Vicinity Thereof

The thin plate member 70 made of metal is disposed radially outside a site on the front end side of the main body section 202. The thin plate member 70 is formed so as to separate the seal member 80 for sealing between the gas sensor 200 and a mounting target body from the main body section 202 of the gas sensor 200. The detailed configurations of the thin plate member 70 and the vicinity thereof will be described referring to FIG. 3B.

As shown in FIG. 3B, the thin plate member 70 has a front end portion 71 formed to be bent in a substantially Z-shape, a tube portion 72 formed in a cylindrical shape along, and approximately parallel to, the axial line 0, a rear end portion 73 formed to be bent in an inverted L-shape, and a groove portion 75 recessed toward the inside in the radial direction with a gap 220 interposed between the groove portion 75 and the outer surface of the site on the front end side of the main body section 202 (in the first example, the metal member 110), between the tube portion 72 and the rear end portion 73. At least one end of the thin plate member 70 is joined to the outer surface of the main body section 202. In the first example, the thin plate member 70 is welded and joined to a front end surface 52a of the brim portion 52 of the metal shell 50 at the front end portion 71. The thin plate member 70 can be formed by a variety of working methods such as deep drawing work or cutting work. In addition, the groove portion 75 may be formed such that a cross section has a rectangular shape. However, any shape is also acceptable.

The seal member 80 is disposed in the groove portion 75 and formed of resin so as to have elasticity. The seal member 80 is deformed by being brought into pressure contact with an inner wall of a sensor mounting hole when the gas sensor 200 is mounted on the mounting target body, and performs sealing between the sensor mounting hole and the gas sensor 200.

Conventionally, since the seal member 80 is disposed in a groove portion formed in a main body section (for example, the metal shell 50), the temperature of the metal shell 50 is directly transmitted to the seal member 80. For this reason, if the metal shell 50 is heated by heat generation of the gas sensor element 131 and thus the temperature of the metal shell 50 exceeds the heatproof temperature of a resin material configuring the seal member 80, a problem that leads to deterioration of the seal member 80 arises.

In the gas sensor 200 of the first example, a thermal pathway in which the heat of the gas sensor element 131 is transmitted to the seal member 80 disposed in the groove portion 75 of the thin plate member 70 includes a first pathway 250, which conducts heat radiation from the main body section 202, and a second pathway 260 which conducts heat from the front end surface 52a of the metal shell 50, which is a joining portion 205, to the thin plate member 70, as shown by arrows in FIG. 3B.

Here, in the first example, the gap 220, functioning as a heat-insulating layer, is interposed between the seal member 80 and the main body section 202. As a result, heat conduction from the main body section 202, that is, heat conduction through the first pathway 250 is reduced, and thus deterioration of the seal member 80 due to heat is suppressed.

Further, since the rear end portion 73 of the thin plate member 70, which is located on the rear end side in the direction of the axial line O, is not joined to the main body section 202, an opening portion 210 making the gap 220 communicate with external air is formed between the rear end portion 73 and the main body section 202. External air enters the gap 220 through the opening portion 210 and air in the gap 220 is cooled by the external air, and thus an increase in the temperature of air in the gap 220 is suppressed. As a result, heat conduction through the first pathway 250 is further reduced, and thus deterioration of the seal member 80 can be suppressed.

Further, the groove portion 75 of the thin plate member 70 is formed at a position distant from the front end surface 52a of the brim portion 52, which is a joining portion where the thin plate member 70 and the outer surface of the main body section 202 are joined to each other. The distant position at which the groove portion 75 is formed may be set to be, for example, at the rear end side at a distance which is greater than or equal to the center (a position that is ½) of a distance d along the direction of the axial line O from the front end surface 52a, which is the joining portion, to the rear end portion 73 of the thin plate member 70. In this way, it is possible to make the distance of the second pathway 260 long, and thus heat conduction through the second pathway 260 is suppressed.

A1-5. Detailed Configuration of the Inside of Metal Shell 50

In the metal shell 50, a tubular ceramic holder 136 made of alumina, a first powder packed bed 137 made of talc powder, a second powder packed bed 138 likewise made of talc powder, and a tubular ceramic sleeve 139 made of alumina are disposed in this order toward the rear end side from the front end side. Further, in the metal shell 50, a tubular metal cup 135 integrated with the gas sensor element 131 is disposed along with the ceramic holder 136 and the first powder packed bed 137. In addition, a caulking ring 58 is disposed between the ceramic sleeve 139 and the rear end portion 55 of the metal shell 50.

The ceramic holder 136 is disposed in the metal cup 135 and engaged with a step portion 51 of the metal shell 50 with the metal cup 135 interposed therebetween at the front end side thereof. The gas sensor element 131 is inserted into the ceramic holder 136. Further, the entirety of the first powder packed bed 137 is disposed in the metal cup 135. In addition, airtightness between the metal shell 50 and the gas sensor element 131 is secured by the existence of the second powder packed bed 138.

The ceramic sleeve 139 is a tubular body having a rectangular axial hole 139a along the axial line O. The plate-shaped gas sensor element 131 is inserted into the rectangular axial hole 139a along the direction of the axial line O, whereby the ceramic sleeve 139 supports the gas sensor element 131. The ceramic sleeve 139 is fixed in the metal shell 50 by performing swaging toward the rear end surface of the ceramic sleeve 139 with the caulking ring 58 interposed therebetween, by bending the rear end portion 55 of the metal shell 50 toward the inside in the radial direction after the ceramic sleeve 139 is mounted in the metal shell 50.

The gas sensor 200 of the first example has a configuration described above. An assembling process of the gas sensor 200 having the above-described configuration will be described below.

A2. Assembling Process of Gas Sensor 200

An assembling process of the gas sensor 200 in the first example will be described below. The element assembly 130, the separator assembly 120, the cover 100, and the thin plate member 70, which configure the gas sensor 200, are prepared. The element assembly 130 and the cover 100 are formed by a variety of known methods. Further, the thin plate member 70 is formed in a shape having the front end portion 71, the rear end portion 73, and the groove portion 75 by performing deep drawing work on a thin flat plate made of metal. Manufacturing of the separator assembly 120 will be described referring to FIGS. 4A, 4B and 4C.

A2-1. Manufacturing Process of Separator Assembly 120

Figure 4A:
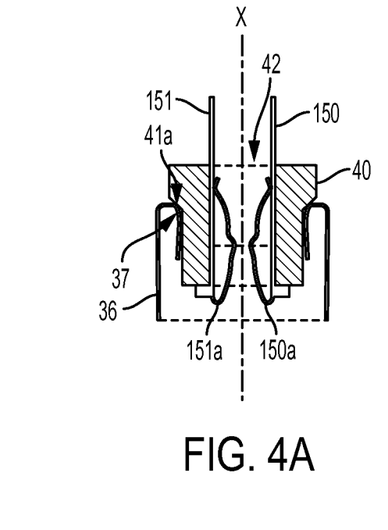
FIGS. 4A, 4B and 4C are explanatory diagrams describing a manufacturing process of a separator assembly 120 in the first example.

FIGS. 4A, 4B and 4C are explanatory diagrams describing a manufacturing process of the separator assembly 120 in the first example. The separator 40, in which the connection terminals 150 and 151 are mounted in the opening 42, and the retaining member 36 subjected to bending work such that the rear end portion 37 is folded radially inward toward the front end side in the direction of an axial line X and having a substantially tubular shape, are prepared. As shown in FIG. 4A, the retaining member 36 is disposed around the separator 40 such that the rear end portion 37 of the retaining member 36 abuts onto a front end facing surface 41a having a tapered shape and formed at the brim portion 41 of the separator 40. In addition, each of the connection terminals 150 and 151 is formed by stamping a long piece-shaped conductive member (a metal piece or the like) by a press or the like and then performing bending work such that the contact portion 150a has a predetermined shape.

Figure 4B:
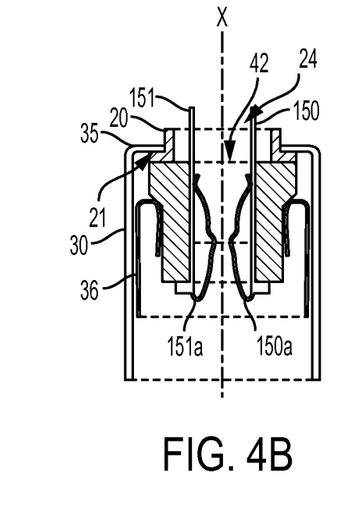

As shown in FIG. 4B, the separator 40 and the retaining member 36 are inserted in the metallic external cylinder 30 having a cylindrical shape, and the rear end 35 of the metallic external cylinder 30 is then swaged with respect to the brim portion 21 of the grommet 20 by a pressing force along the direction of an axial line X. As a result, the separator 40 is retained and fixed by the metallic external cylinder 30 and the retaining member 36. In addition, in the swaging, the retaining member 36 and the separator 40 are retained by a retaining jig (not shown).

Figure 4C:
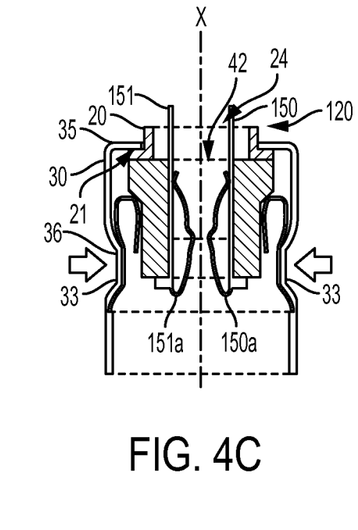

As shown in FIG. 4C, a substantially central portion of the metallic external cylinder 30 is swaged toward the inside in the radial direction from the outside in the radial direction, whereby the swaged portion 33 is formed, and thus the retaining member 36 is fixed to the metallic external cylinder 30. In addition, the retaining member 36 may be fixed to the metallic external cylinder 30 by welding and may also be fixed by further performing welding after swaging. In this way, the separator assembly 120 is fabricated.

A2-2. Assembling of Gas Sensor 200

Figure 5A:
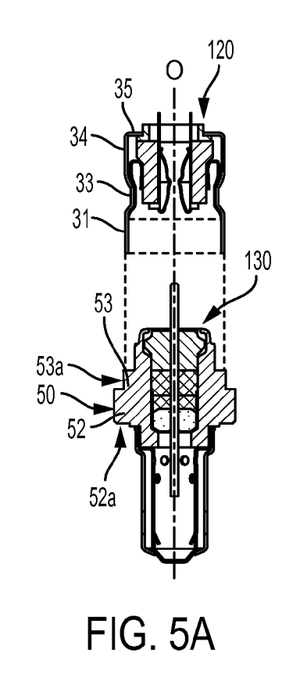
FIGS. 5A, 5B, 5C and 5D are explanatory diagrams describing a manufacturing process of the gas sensor 200 in the first example.

FIGS. 5A, 5B, 5C and 5D are explanatory diagrams describing a manufacturing process of the gas sensor 200 in the first example. As shown in FIG. 5A, the separator assembly 120 is inserted at a rear end of the element assembly 130 from the front end portion 31 side and the front end portion 31 is then swaged with respect to a side surface 53a of the step portion 53 from the outside in the radial direction toward the inside in the radial direction. As a result, the separator assembly 120 is fixed to the metal shell 50 of the element assembly 130.

Figure 5B:
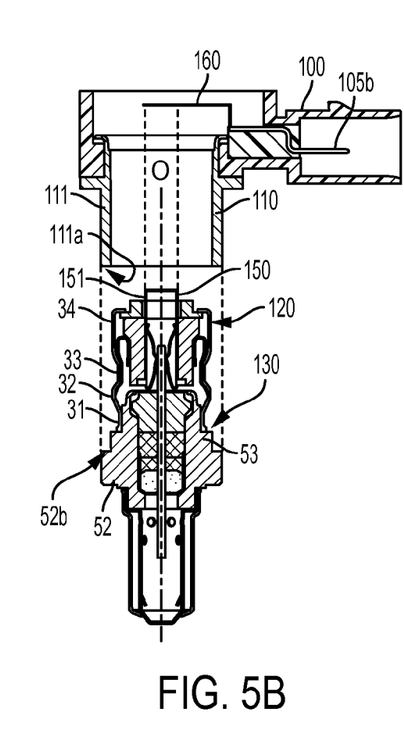

As shown in FIG. 5B, the cover 100, except for the lid section 109, is assembled. Specifically, the cover 100 is inserted at a rear end of the element assembly 130 along the axial line O from the front end side of the metal member 110 until a front end surface 111a of the metal member 110 and the rear end surface 52b of the brim portion 52 of the metal shell 50 abut each other, and the first tube portion 111 of the metal member 110 and the step portion 53 of the metal shell 50 are welded and joined to each other, and thus the cover 100 is assembled to the element assembly 130. In addition, during the assembling of the cover 100, the relative positional relationship between the cover 100 and the connection terminals 150 and 151 is adjusted such that the connector terminal 105b is electrically connected to the connection terminals 150 and 151.

Figures 5C, 5D:
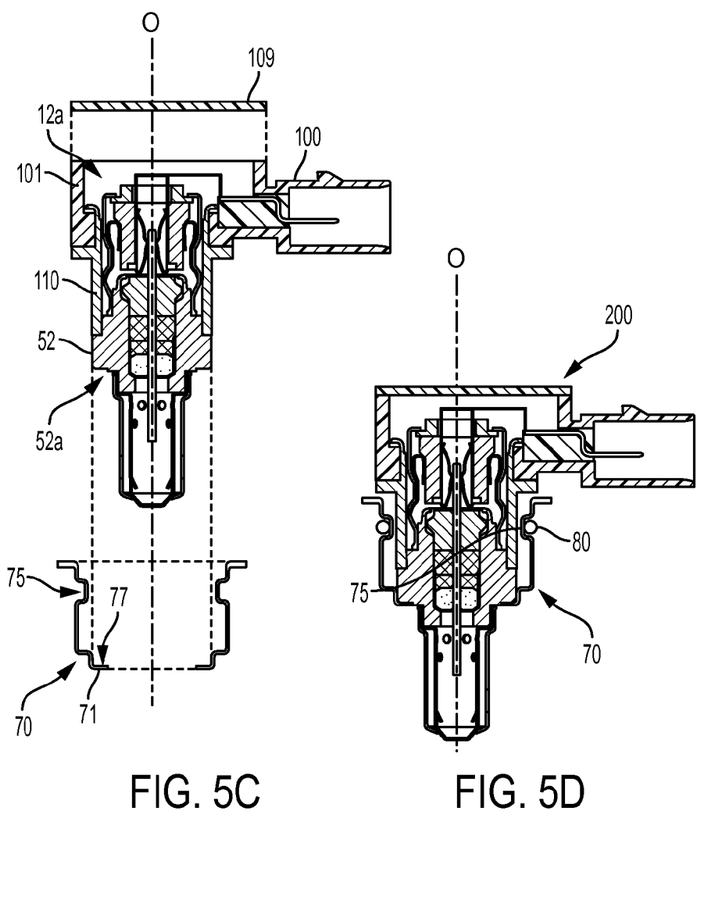

As shown in FIG. 5C, the lid section 109 is assembled so as to cover an opening 12a of the cover 100 and also the thin plate member 70 is assembled to the element assembly 130. Specifically, the rear end side of the thin plate member 70 is inserted from the front end side of the element assembly 130 along the axial line O until a joining portion 77 of the front end portion 71 of the thin plate member 70 formed in a substantially tubular shape and the front end surface 52a of the brim portion 52 of the metal shell 50 abut each other, and contact portions of the joining portion 77 and the brim portion 52 are then welded and joined to each other.

As shown in FIG. 5D, the seal member 80 is disposed in the groove portion 75 of the thin plate member 70, and thus the gas sensor 200 is completed.

According to the gas sensor 200 of the first example described above, the gas sensor 200 includes the thin plate member 70, which is disposed radially outside the site on the front end side of the main body section, has the groove portion 75 recessed toward the inside in the radial direction with the gap 220 interposed between the groove portion 75 and the outer surface of the site on the front end side, and is joined to the outer surface of the main body section. The seal member 80, which is brought into pressure contact with the inner wall of the sensor mounting hole when the gas sensor is mounted on the mounting target body, is disposed in the groove portion 75 of the thin plate member 70. Therefore, conduction of heat of the gas sensor element 131 to the groove portion 75 of the thin plate member 70 can be suppressed by the gap 220, that is, an air layer formed between the thin plate member 70 and the main body section. Further, since the thin plate member 70 is formed in the shape of a thin plate, heat-transfer performance from the main body section to the thin plate member 70 can be reduced. Accordingly, deterioration of the seal member 80 disposed in the groove portion due to thermal influence by heat generation of the gas sensor element 131 can be suppressed.

Further, according to the gas sensor 200 of the first example, since the thin plate member 70 is mounted on the metal shell 50, heat generated in the gas sensor element 131 is transmitted to the seal member 80 through the metal shell 50 and the thin plate member 70. Therefore, it is possible to make a pathway in which heat is transmitted from the gas sensor element 131 to the seal member 80 long compared to a case where the thin plate member 70 is not provided. Accordingly, thermal insulation performance from the main body section to the seal member 80 can be improved. Further, since one end of the thin plate member 70 is joined to the front end surface of the brim portion of the metal shell 50, the metal shell 50 is supported by the thin plate member 70. Therefore, thermal insulation performance from the main body section to the seal member 80 can be improved, and even if weld strength between the metal shell 50 and the thin plate member 70 is reduced, and thus peel-off occurs in the joining portion, falling of the metal shell 50 into the mounting hole of the mounting target body can be suppressed.

Further, according to the gas sensor 200 of the first example, the groove portion 75 is formed at a position distant from the joining portion where the thin plate member 70 and the outer surface of the main body section are joined to each other. Therefore, it is possible to make a heat transfer pathway from the main body section to the groove portion long, and thus thermal insulation performance from the main body section to the seal member 80 can be improved.

Further, according to the gas sensor 200 of the first example, one of the end portions of the thin plate member 70 is not joined and is in an open state. Therefore, it is possible to take in external air from the opening portion 210 and air in the gap 220 can be cooled by the external air. Accordingly, thermal insulation performance between the gas sensor element 131 and the seal member 80 can be improved.

Further, in the horizontal lead-out type gas sensor 200 as in the first example, since a reduction in size in the direction of the axial line is desired, the seal member 80 and a heat generation site of the gas sensor element 131 inevitably come close to each other. However, according to the gas sensor 200 of the first example, an air layer can be interposed between the main body section which directly receives thermal influence of heat generation of the gas sensor element 131 and the seal member 80. Accordingly, deterioration of the seal member 80 due to thermal influence by heat generation of the gas sensor element 131 can be suppressed.

B. SECOND EXAMPLE

B1. Schematic Configuration of Gas Sensor 200*a*

Figure 6:
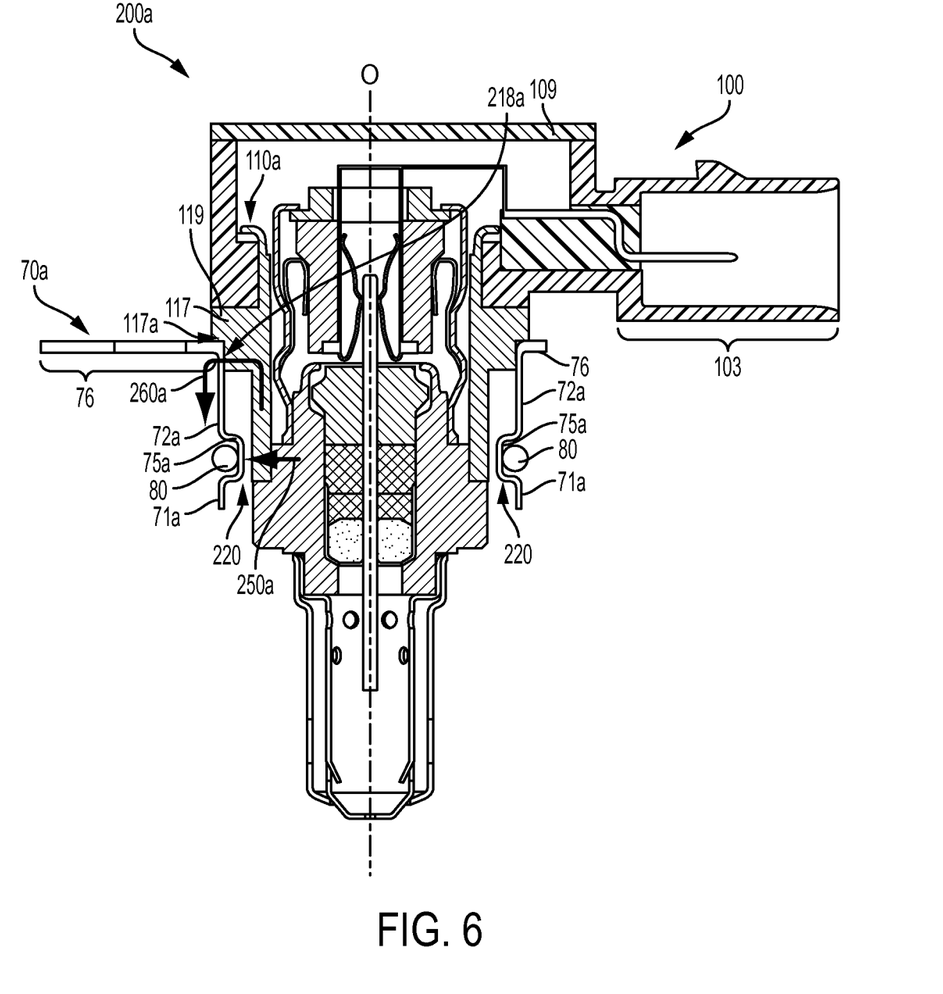
FIG. 6 is a cross-sectional view showing the schematic configuration of a gas sensor 200*a* in a second example.

FIG. 6 is a cross-sectional view showing the schematic configuration of a gas sensor 200*a* in the second example. Since the gas sensor 200*a* has the same configuration as that of the gas sensor 200 of the first example, except for the configurations of a flange portion 119 of a metal member 110*a* and a thin plate member 70*a*, description will be made using the same reference numerals used in the first example.

The flange portion 119 of the metal member 110*a* has a first brim portion 218 formed on the front end side thereof and a second brim portion 117 which is formed on the rear end side of the first brim portion 218 and has a larger diameter than the first brim portion 218.

The thin plate member 70*a* is formed of a thin plate made of metal and has a front end portion 71*a* formed in a cylindrical shape approximately parallel to an axial line O, a tube portion 72*a*, a groove portion 75*a* formed in the shape of a radially inward recess with the gap 220 disposed radially outside the metal member 110*a* and the metal shell 50 which configure the main body section, between the front end portion 71*a* and the tube portion 72*a*, and a flange 76 extending from a rear end of the tube portion 72*a* toward the outside in the radial direction. A plurality of holes (not shown) is formed in the flange 76, and a screw is inserted in each hole and screwed into a threaded hole provided in the mounting target body, whereby the gas sensor 200*a* can be mounted on the mounting target body.

The thin plate member 70*a* is joined to a side surface 218*a* of the first brim portion 218 and a front end surface 117*a* of the second brim portion 117 at a bend portion where the tube portion 72*a* and the flange 76 are switched, thereby being fixed to the gas sensor 200*a*. As a joining method, for example, weld joining can be used.

In the gas sensor 200*a*, a thermal pathway in which heat of the gas sensor element 131 is transmitted to the seal member 80 disposed in the groove portion 75*a* of the thin plate member 70*a* includes a first pathway 250*a*, which conducts heat radiation from a main body section of the gas sensor 200*a*, and a second pathway 260*a*, which conducts heat from the metal member 110*a* that is a joining portion to the thin plate member 70*a*, as shown in arrows.

Here, in the second example, the gap 220, functioning as a heat-insulating layer, is interposed between the seal member 80 and the main body section. Therefore, according to the gas sensor 200*a*, heat conduction from the main body section 202, that is, heat conduction through the first pathway 250*a* is reduced, and thus deterioration of the seal member 80 due to heat is suppressed.

Further, the groove portion 75*a* of the thin plate member 70*a* is formed at a position distant from the flange portion 119 that is a joining portion where the thin plate member 70*a* and the outer surface of the main body section are joined to each other. The distant position at which the groove portion 75*a* is formed may be set to be, for example, at the front end side at a distance which is greater than or equal to the center (a position that is ½) of a distance along the direction of the axial line O from the first brim portion 218, which is the joining portion, to a front end of the front end portion 71*a* of the thin plate member 70*a*. In this way, it is possible to make the distance of the second pathway 260*a* long, and thus heat conduction through the second pathway 260*a* is suppressed.

Further, according to the gas sensor 200*a* of the second example, the thin plate member 70*a* is joined to the metal member 110*a* disposed between the metal shell 50 and the cover 100. Therefore, it is possible to make a heat transfer pathway from the gas sensor element to the seal member 80 long and it is possible to interpose a plurality of members in the heat transfer pathway. Accordingly, thermal insulation performance from the main body section to the seal member can be improved.

Further, according to the gas sensor 200*a* of the second example, since the thin plate member includes the flange portion, it is not necessary to individually prepare a mold for the flange portion, and it is possible to cope with changes in various configurations such as a mounting direction (a mounting angle) of the gas sensor, a mounting depth, the shape of a flange, or the position of a mounting hole merely by changing the configuration of the thin plate member, and thus a reduction in cost can be attained.

C. THIRD EXAMPLE

C1. Schematic Configuration of Gas Sensor 200*b*

Figure 7:
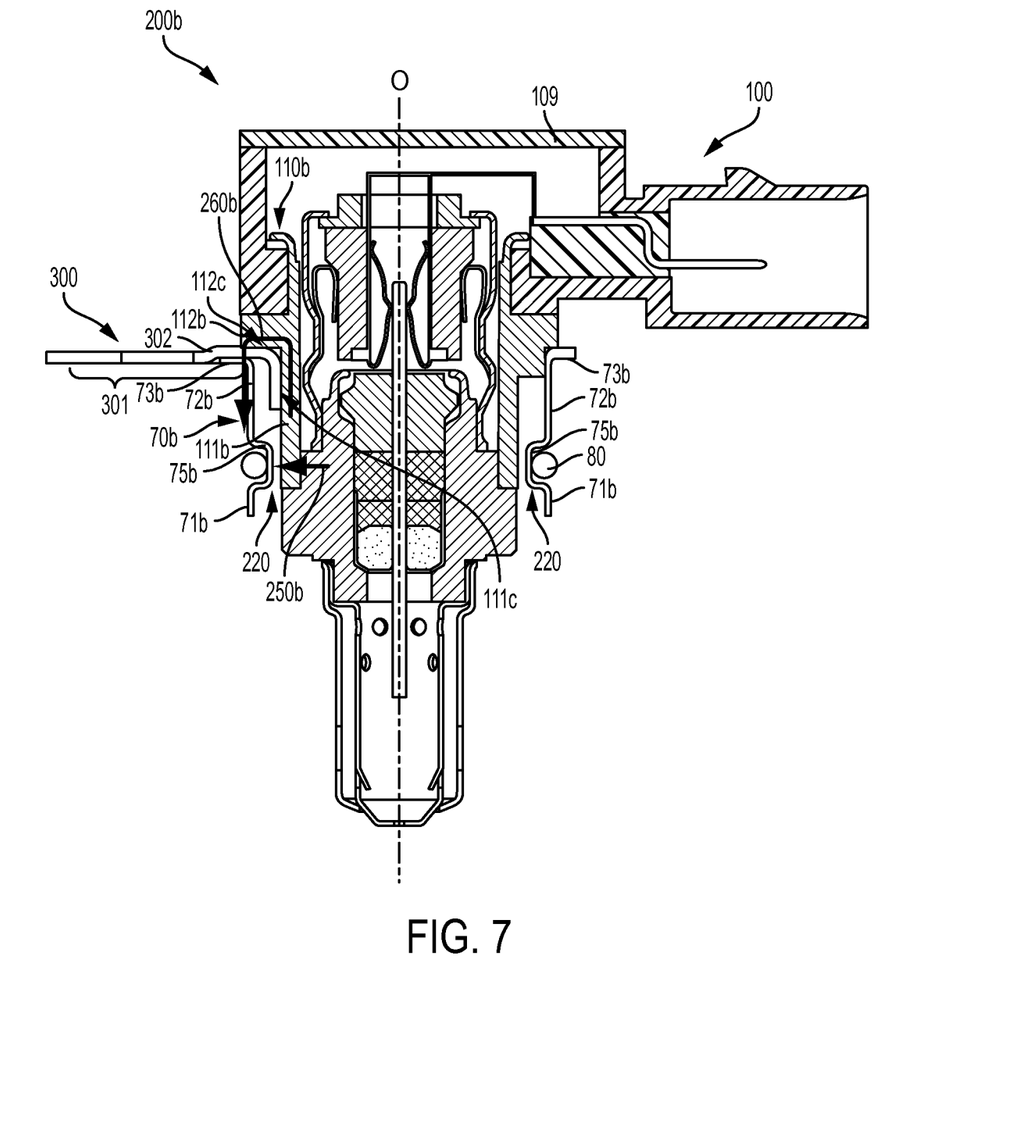
FIG. 7 is a cross-sectional view showing the schematic configuration of a gas sensor 200*b* in a third example.

FIG. 7 is a cross-sectional view showing the schematic configuration of a gas sensor 200*b* according to the third example. Since the gas sensor 200*b* has the same configuration as that of the gas sensor 200 of the first example, except for a newly added flange 300 and the configurations of a thin plate member 70*b* and a metal member 110*b*, description will be made using the same reference numerals used in the first example.

The metal member 110*b* has a flange portion 112*b* having a shape in which the flange portion 112 of the metal member 110 in the first example is omitted. Other configurations are the same as those of the metal member 110 in the first example.

The flange 300 has an extension portion 301 extending toward the outside in the radial direction and an end portion 302 formed at a radially inside end portion of the extension portion 301 and formed to be bent toward the front end side in the direction of the axial line O. The end portion 302 is joined to a front end surface 112*c* of the flange portion 112*b* and a side surface 111*c* of a first tube portion 111*b*. As a joining method, for example, weld joining can be used.

The thin plate member 70*b* is formed of a thin plate made of metal and has a front end portion 71*b* formed in a cylindrical shape approximately parallel to the axial line O, a tube portion 72*b*, a rear end portion 73*b* formed to be bent toward the outside in the radial direction at the rear end side of the tube portion 72*b*, and a groove portion 75*b* formed between the front end portion 71*b* and the tube portion 72*b*. The groove portion 75*b* is formed in the shape of a radially inward recess with the gap 220 disposed radially outside the metal member 110*a* and the metal shell 50 which configure the main body section.

The thin plate member 70*b* is joined to the front end surface of the end portion 302 at the rear end portion 73*b*. As a joining method, for example, weld joining can be used.

In the gas sensor 200*b*, a thermal pathway in which heat of the gas sensor element 131 is transmitted to the seal member 80 disposed in the groove portion 75*b* of the thin plate member 70*b* includes a first pathway 250*b*, which conducts heat radiation from a main body section of the gas sensor 200*b*, and a second pathway 260b, which conducts heat from the flange 300 that is a joining portion to the thin plate member 70b, as shown in arrows.

Here, in the third example, the gap 220 functioning as a heat-insulating layer is interposed between the seal member 80 and the main body section. Therefore, according to the gas sensor 200b, heat conduction from the main body section, that is, heat conduction through the first pathway 250b is reduced, and thus deterioration of the seal member 80 due to heat is suppressed.

Further, the groove portion 75b of the thin plate member 70b is formed at a position distant from the flange 300 that is a joining portion where the thin plate member 70b and the outer surface of the main body section are joined to each other. The distant position at which the groove portion 75b is formed may be set to be, for example, at the front end side at a distance which is greater than or equal to the center (a position that is about ½) of a distance along the direction of the axial line O from the end portion 302 of the flange 300 which is the joining portion, to a front end of the front end portion 71b of the thin plate member 70b. In this way, it is possible to make the distance of the second pathway 260b long, and thus heat conduction through the second pathway 260b is suppressed.

Further, in the second pathway 260b, the metal member 110b, the flange 300, and the thin plate member 70b are interposed between the metal shell 50, which easily receives thermal influence by heat generation of the gas sensor element 131 and the seal member 80. Therefore, it is possible to increase the number of members which are included in the pathway. Generally, since heat conduction performance between different members is reduced, the greater the number of members which are interposed in the second pathway 260b is, the further the heat conduction through the second pathway 260b can be suppressed. Further, if heat is transmitted to the flange 300, since the heat also conducts to the extension portion 301, a heat radiation area can be increased, and thus heat conduction to the seal member 80 can be further suppressed.

Further, according to the gas sensor 200b of the third example, since the thin plate member is assembled to the flange, it is possible to make a heat transfer pathway from the gas sensor element to the seal member long and it is possible to interpose a plurality of members in the heat transfer pathway. Accordingly, thermal insulation performance from the main body section to the seal member can be improved.

D. MODIFIED EXAMPLES

In the first to third examples described above, description has been made using the configuration in which the seal member is disposed in the groove portion of the thin plate member. However, the present invention is not limited thereto. Other application examples of the thin plate member and the vicinity thereof will be described below referring to FIGS. 8A, 8B, 8C, 8D and 8E. FIGS. 8A, 8B, 8C, 8D and 8E are explanatory diagrams describing the configurations of the thin plate member and the vicinity thereof in modified examples.

Figure 8A:
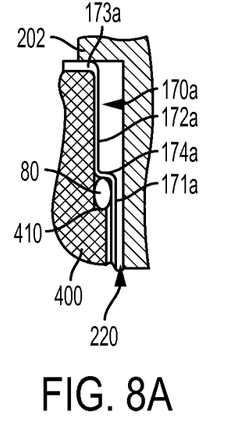
FIGS. 8A, 8B, 8C, 8D and 8E are explanatory diagrams showing the schematic configurations of a thin plate member and the vicinity thereof in modified examples.

As shown in FIG. 8A, a thin plate member 170a is formed of a thin plate made of metal and has a tube portion 172a formed in a cylindrical shape approximately parallel to an axial line, a bend portion 174a extending in a diameter reducing manner from the tube portion 172a toward the inside in the radial direction, a front end portion 171a extending from the bend portion 174a toward the front end side in the direction of the axial line, and a rear end portion 173a which extends from the bend portion 174a toward the rear end side in the direction of the axial line and is joined to the main body section. In other words, the bend portion 174a is formed in the shape of a bend extending in a diameter expansion manner from a rear end of the front end portion 171a of the tube portion 172a toward the outside in the radial direction. Furthermore, the bend portion 174a which extends toward the rear end side in the direction of the axial line and is connected toward the rear end portion 173a. The front end portion 171a is disposed radially outside the metal member 110a and the metal shell 50, which configure the main body section 202, with the gap 220 interposed therebetween.

The seal member 80 is disposed so as to come into contact with the bend portion 174a, and when the gas sensor 200 is mounted on a mounting target body 400, the seal member 80 is deformed by being engaged with and brought into pressure contact with a step portion 410 of the mounting target body 400 and performs sealing between the mounting target body 400 and the gas sensor 200.

Figure 8B:
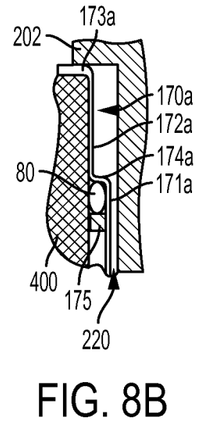

As shown in FIG. 8B, the thin plate member 170a is formed of a thin plate made of metal and has the tube portion 172a formed in a cylindrical shape approximately parallel to an axial line, the bend portion 174a extending in a diameter reducing manner from the tube portion 172a toward the inside in the radial direction, the front end portion 171a extending from the bend portion 174a toward the front end side in the direction of the axial line, and the rear end portion 173a which extends from the bend portion 174a toward the rear end side in the direction of the axial line and is joined to the main body section 202. The front end portion 171a is disposed radially outside the metal member 110a and the metal shell 50, which configure the main body section 202, with the gap 220 interposed therebetween. Further, a ring-shaped collar 175 is fixed to the outer surface of the front end portion 171a.

The seal member 80 is disposed so as to come into contact with the bend portion 174a and the collar 175, in other words, so as to be supported by the bend portion 174a and the collar 175, and when the gas sensor 200 is mounted on the mounting target body 400, the seal member 80 is deformed by being brought into pressure contact with the mounting target body 400 and performs sealing between the mounting target body and the gas sensor 200.

Figure 8C:
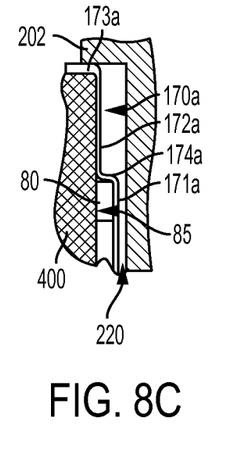

As shown in FIG. 8C, the thin plate member 170a is formed of a thin plate made of metal and has the tube portion 172a formed in a cylindrical shape approximately parallel to an axial line, the bend portion 174a extending in a diameter reducing manner from the tube portion 172a toward the inside in the radial direction, the front end portion 171a extending from the bend portion 174a toward the front end side in the direction of the axial line, and the rear end portion 173a which extends from the bend portion 174a toward the rear end side in the direction of the axial line and is joined to the main body section 202. The front end portion 171a is disposed radially outside the metal member 110a and the metal shell 50, which configure the main body section 202, with the gap 220 interposed therebetween.

The seal member 80, which is disposed so as to come into contact with the bend portion 174a, has a crease portion 85 having creases in the surface facing the mounting target body, and when the gas sensor 200 is mounted on the mounting target body 400, the creases of the crease portion 85 are brought into pressure contact with the mounting target body 400, whereby the seal member 80 is deformed, thereby performing sealing between the mounting target body 400 and the gas sensor 200. In addition, in a case of using the seal member 80 having such a shape, since it is not necessary for the seal member 80 to be engaged with a step portion of the mounting target body 400, it becomes possible to broaden the option of a mounting place such as application to a site on a cylindrical surface, for example.

Figure 8D:
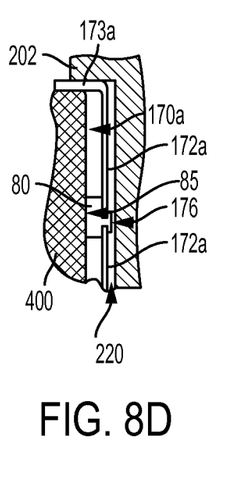

As shown in FIG. 8D, the thin plate member 170a is formed of a thin plate made of metal and has the tube portion 172a formed in a cylindrical shape approximately parallel to an axial line and the rear end portion 173a which extends from the rear end of the tube portion 172a toward the outside in the radial direction and is joined to the main body section 202. The tube portion 172a is disposed radially outside the metal member 110a and the metal shell 50, which configure the main body section 202, with the gap 220 interposed therebetween. The tube portion 172a has a through-hole 176.

The seal member 80 has the crease portion 85 having creases in the surface facing the mounting target body 400 and is disposed to be fitted into the through-hole 176. When the gas sensor 200 is mounted on the mounting target body, the creases of the crease portion 85 are brought into pressure contact with the mounting target body 400, whereby the seal member 80 is deformed, thereby performing sealing between the mounting target body 400 and the gas sensor 200. In addition, in a case of using the seal member 80 having such a shape, since it is not necessary for the seal member 80 to be engaged with a step portion of the mounting target body 400, it becomes possible to broaden the option of a mounting place such as application to a site on a cylindrical surface, for example. Further, since it is not necessary to dispose a bend portion (the bend portion 174a: refer to FIGS. 8A, 8B and 8C), the through-hole 176 may be provided in any location of the metal member 110a, and thus it becomes possible to further broaden the option of a mounting place.

Figure 8E:
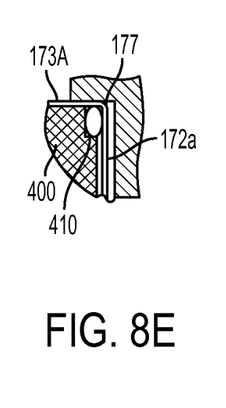

As shown in FIG. 8E, the thin plate member 170a is formed of a thin plate made of metal and has the tube portion 172a formed in a cylindrical shape approximately parallel to an axial line, the rear end portion 173a extending from a rear end of the tube portion 172a toward the outside in the radial direction, and a bend portion 177 which is a connection portion between the tube portion 172a and the rear end portion 173a and is joined to the main body section. The tube portion 172a is disposed radially outside the metal member 110a and the metal shell 50, which configure the main body section 202, with the gap 220 interposed therebetween.

The seal member 80 is disposed so as to come into contact with the bend portion 177, and when the gas sensor 200 is mounted on the mounting target body 400, the seal member 80 is deformed by being engaged with and brought into pressure contact with the step portion 410 of the mounting target body 400 and performs sealing between the mounting target body and the gas sensor 200.

Various examples of the invention have been described above. However, the invention is not limited to these examples and can take various configurations within a scope which does not depart from the gist of the invention. For example, in the examples described above, the metal member 110 has been described as an example of the base section. However, the invention is not limited thereto and the base section may be configured of heat-resistant resin such as PPS.

The invention has been described in detail with reference to the above embodiments. However, the invention should not be construed as being limited thereto. It should further be apparent to those skilled in the art that various changes in form and detail of the invention as shown and described above may be made. It is intended that such changes be included within the spirit and scope of the claims appended hereto.

This application is based on Japanese Patent Application No. 2012-118872 filed May 24, 2012 and Japanese Patent Application No. 2013-105767 filed May 20, 2013, both of which are incorporated herein by reference in their entirety.

What is claimed is:

1. A gas sensor comprising:
   a gas sensor element having a detecting portion which detects a specific gas component in gas to be measured, wherein the detecting portion is disposed at a front end side in a direction of an axial line of the gas sensor element;
   a main body section which surrounds a circumference in a radial direction of the gas sensor element, wherein a front end side portion of the main body section is configured to be inserted into a gas sensor mounting hole of a mounting target body, and wherein a rear end side portion of the main body section is configured to be disposed outside the gas sensor mounting hole when the gas sensor is mounted on the mounting target body;
   a thin plate member which is disposed radially outside the front end side portion of the main body section with a gap interposed between the thin plate member and an outer surface of the front end side portion of the main body section, wherein at least one end of the thin plate member is joined to an outer surface of the main body section; and
   a seal member which is disposed between the thin plate member and the mounting target body and which is brought into pressure contact with the mounting target body when the gas sensor is mounted on the mounting target body.

2. The gas sensor as claimed in claim 1, wherein the main body section has a metal shell which surrounds the circumference in the radial direction of the gas sensor element, wherein a front end side of the metal shell is configured to be inserted into the gas sensor mounting hole of the mounting target body when the gas sensor is mounted on the mounting target body, and wherein the thin plate member is joined to the metal shell.

3. The gas sensor as claimed in claim 2, wherein the metal shell has a brim portion which protrudes toward an outside in the radial direction of the gas sensor element, and wherein one end of the thin plate member is joined to a surface on the front end side of the brim portion.

4. The gas sensor as claimed in claim 1, wherein the main body section has a metal shell which surrounds the circumference in the radial direction of the gas sensor element, wherein a front end side of the metal shell is configured to be inserted into the gas sensor mounting hole of the mounting target body when the gas sensor is mounted on the mounting target body, wherein a cover is disposed on a rear end side of the metal shell wherein the gas sensor further includes a tubular base body which is joined to an outer periphery on a rear end portion of the metal shell and which connects the metal shell and the cover, and wherein the thin plate member is joined to the tubular base body.

5. The gas sensor as claimed in claim 1, wherein the main body section has a metal shell which surrounds the circumference in the radial direction of the gas sensor element, wherein a front end side of the metal shell is configured to be inserted into the gas sensor mounting hole of the mounting target body when the gas sensor is mounted on the mounting target body, wherein the gas sensor further includes a flange which is attached to the metal shell and which is configured to be attached to the mounting target body, and wherein the thin plate member is attached to the flange.

6. The gas sensor as claimed in claim 1, wherein the main body section has a metal shell which surrounds the circumference in the radial direction of the gas sensor element,
   wherein a front end side of the metal shell is configured to be inserted into the gas sensor mounting hole of the mounting target body when the gas sensor is mounted on the mounting target body,
   wherein a cover is disposed on a rear end side of the metal shell, and
   wherein the cover has a signal extraction section which extends in a direction intersecting the direction of the axial line.

7. The gas sensor as claimed in claim 1, wherein the thin plate member comprises:
   a tube portion which is disposed so as to surround a circumference in the radial direction of the main body section; and
   a bend portion which extends from a rear end of the tube portion toward an outside in the radial direction of the main body section, and
   wherein the seal member is disposed in contact with the bend portion.

8. The gas sensor as claimed in claim 1, wherein the thin plate member has a groove portion recessed toward an inside in a radial direction of the main body section, and
   wherein the seal member is disposed within the groove portion.

9. The gas sensor as claimed in claim 8, wherein the groove portion is formed at a position distant from a joining portion where the thin plate member and the outer surface of the main body section are joined to each other.

10. The gas sensor as claimed in claim 1, wherein the thin plate member comprises:
    a tube portion which is disposed so as to surround a circumference in the radial direction of the main body section,
       wherein the tube portion comprises a front end portion; and
    a bend portion which extends from a rear end of the front end portion of the tube portion toward an outside in the radial direction of the main body section, and
    wherein the seal member is disposed in contact with the bend portion.

11. The gas sensor as claimed in claim 1, wherein the thin plate member comprises:
    a tube portion which is disposed so as to surround a circumference in the radial direction of the main body section,
    wherein the tube portion comprises a through-hole, and
    wherein the seal member is configured to be fitted into the through-hole.

12. The gas sensor as claimed in claim 1, wherein one end of the thin plate member is joined to the outer surface of the main body section and the other end of the thin plate member is not joined to the outer surface of the main body section.

\* \* \* \* \*